(12) United States Patent
Younis et al.

(10) Patent No.: US 7,115,563 B2
(45) Date of Patent: Oct. 3, 2006

(54) COMPOSITION AND ITS THERAPEUTIC USE

(75) Inventors: Rafeda M. A. Younis, Sharjah (AE);
Karam M. H. Al Sari, Sharjah (AE);
Saad M. H. Al Sari, Sharjah (AE);
Ahmad M. H. Al Sari, Sharjah (AE)

(73) Assignees: Insignion Holding Limited, Hamilton HM (BB); Veritron Limited, London (GB)

( * ) Notice: Subject to any disclaimer, the term of this patent is extended or adjusted under 35 U.S.C. 154(b) by 28 days.

(21) Appl. No.: 10/447,770

(22) Filed: May 29, 2003

(65) Prior Publication Data

US 2004/0142852 A1    Jul. 22, 2004

Related U.S. Application Data

(60) Provisional application No. 60/407,373, filed on Aug. 30, 2002.

(30) Foreign Application Priority Data

May 29, 2002    (GB)    ................... 0212405.5

(51) Int. Cl.
*A61K 38/28*    (2006.01)
*A61K 31/51*    (2006.01)
(52) U.S. Cl. .......................... 514/3; 514/276; 514/350; 514/356; 514/474
(58) Field of Classification Search ............... None
See application file for complete search history.

(56) References Cited

U.S. PATENT DOCUMENTS

| | | | |
|---|---|---|---|
| 2,707,696 A | 5/1955 | Worne | |
| 5,461,030 A * | 10/1995 | Lindenbaum | 514/4 |
| 5,591,709 A * | 1/1997 | Lindenbaum | 514/4 |
| 6,399,381 B1 * | 6/2002 | Blum et al. | 435/404 |
| 6,692,961 B1 * | 2/2004 | Judd et al. | 435/406 |

FOREIGN PATENT DOCUMENTS

| | | |
|---|---|---|
| EP | 0 771 555 A2 | 5/1995 |
| GB | 804293 | 3/1956 |
| GB | 957020 | 6/1960 |
| GB | 1 603 639 | 7/1977 |
| GB | 2 179 551 A | 8/1985 |
| WO | WO 95/27501 | 4/1995 |
| WO | WO 96/37229 | 4/1996 |
| WO | WO 97/40813 | 4/1997 |
| WO | WO 98/42188 | 3/1998 |
| WO | WO 00/50045 | 2/2000 |
| WO | WO 01/03681 | 1/2001 |
| WO | WO01/66085 | 9/2001 |
| WO | WO 01/66085 A2 | 9/2001 |

OTHER PUBLICATIONS

Abstract of Chinese Patent Number: CN1185975.
Abstract of Chinese Patent Number: CN1213534.
Abstract of Chinese Patent Number: CN1322537.
Abstract of Japanese Patent Number: JP19840055333.
Abstract of Romanian Patent Number: RO80304 A.
Abstract of Russian Journal: "Byulleten Eksperimental'noi Biologii I Meditsiny" (1976) 81(5), 560-1, Coden: Bebmae; ISSN: 0365-9615.
Abstract of Russian Journal: "Pediatriya" (1964), (7), pp. 11-16.
Abstract of Russian Journal: "Problemy Gematologii I Perelivaniya Krovi" (1973) vol. 18, No. 7, pp. (28-32).
Abstract of Soviet Union Patent Number: SU19833537801.
Abstract of Soviet Union Patent Number: SU19874345008.
Abstract of Soviet Union Patent Number: SU19925054016.
Abstract of Ukraine Journal: "Ukrainskii Biokhimicheskii Zhurnal" (1979) vol. 51 No. 1 pp. (27-30).

* cited by examiner

*Primary Examiner*—B. Dell Chism
(74) *Attorney, Agent, or Firm*—McDonnell Boehnen Hulbert & Berghoff LLP

(57) ABSTRACT

A composition having a variety of therapeutic and cosmetic uses comprises:
(i) a vitamin;
(ii) a metal salt that provides metal ions in vivo; and
(iii) insulin or a growth hormone.

Such a composition is useful for treating, for example, genetic disorders, skin diseases, cancer and viral infections.

18 Claims, No Drawings

COMPOSITION AND ITS THERAPEUTIC USE

This application claims priority to U.S. Provisional Application Ser. No. 60/407,373, filed Aug. 30, 2002, and to Great Britain Application No. GB 0212405.5, filed May 29, 2002, the disclosures of which are incorporated herein in their entirety.

BACKGROUND OF THE INVENTION

1. Field of the Invention

This invention relates to a composition comprising primarily natural products and to its use in therapy, especially of genetic disorders, viral diseases, cancer and AIDS. The composition is also useful as a cosmetic.

2. Description of the Related Art

Despite decades of research, the treatment of cancer remains unsatisfactory. Surgery may be used to remove a solid tumour, but metastasis or recurrence of the cancer is common. Treatment with drugs, or chemotherapy, is usually non-specific, and is associated with undesirable side-effects, including damage to the immune system. Cell destruction by cytotoxic drugs follows first order kinetics, i.e. it reduces a constant percentage and not a constant number of cancer cells. Thus, the same dose which reduces the number of cancer cells from $10^8$ to $10^7$ is required to reduce the number from $10^3$ to $10^2$. Therefore, it is difficult to eradicate the last portion of any tumour solely by chemotherapy without causing serious toxicity.

Radiotherapy may be more localised, but is still dangerous to the patient and cannot avoid recurrence; the very localisation of the treatment means that there may be many cancerous or pre-cancerous cells that are unaffected by it, even if damage to healthy cells can be avoided. Surgery, radiation treatment and chemotherapy all leave residual tumour tissue following the completion of therapy. Both radiotherapy and chemotherapy depress the immune system of the patient which can in turn reduce the effectiveness of any treatment.

Similarly, the treatment of AIDS remains unsatisfactory. Drug treatment can provide some remission of symptoms, but is liable to cause side-effects. Thus, there is no effective long-term treatment. Further, the fact that AIDS patients are immuno-compromised remains a major problem for conventional therapy.

In addition to cancer and AIDS, there are many conditions that can only be addressed by chemotherapy associated with side-effects, owing to the unspecific nature of the drugs that are used. These conditions include skin diseases such as psoriasis, pemphigus and scleroderma. Further, there are veterinary conditions where there is no effective treatment, including Newcastle disease.

Conditions of the type described above may be associated with a genetic disorder, e.g. some failure in the process whereby genes are translated into proteins, in vivo. It is known that a change of just one amino acid in a protein may be associated with disease, e.g. as in sickle cell anaemia. Proliferative conditions and cancer, among others, may be associated with an error in the sequence of events leading from organisation of genes to production of protein.

SUMMARY OF THE INVENTION

The present invention is based on the surprising discovery that the use of one or more natural products, i.e. materials that are present in the body in vivo or are at least well tolerated by it, are effective in the treatment of diseases of the type described above. The nature of the materials is such that the novel medicament can be administered systemically, without causing major side-effects. Nevertheless, the effect of the medicament may be enhanced or supported by the use of certain further materials.

According to the present invention, a medicament comprises one or more of the following components:
- (i) an antioxidant or vitamin;
- (ii) metal ions; and
- (iii) an agent that enhances the ability of a cell to take up extracellular components.

As will be evident from the data presented below, the use of all the given components in combination is of remarkable utility in therapy. It will be appreciated by one skilled in the art that the effect of these components may be independent or interdependent, and that this is not inconsistent with the nature of the discovery that has been made. Thus, it will be appreciated that an effective agent for use in therapy, according to the present invention, may comprise only one of the given components (i), (ii) and (iii), or any combination of them, i.e. (i) and (ii), (i) and (iii), (ii) and (iii) or (i), (ii) and (iii). Alternatively or in addition, it may comprise one or more of these components in combination with any other component described herein, e.g. an aqueous composition comprising camomile, for injection, or a combination of antioxidant and antihistamine.

The invention has, as an object, the avoidance of gene mutation, and the prevention of rapid reproduction of mutated cells.

Without wishing to be bound by theory, the effect of the components used in the present invention may be to regulate and/or correct the steps leading to expression of proteins, e.g. in immuno-compromised cells, in tumours or in cells that are otherwise acting abnormally. For example, it may be that a component such as component (i) "normalises" cells, possibly by correcting a differentiation gene or by activating a gene that lyses abnormal cells. According to the invention, this component is provided in a form that can act on the affected cells. The possibility that cells are normalised would help explain why cells that are already normal remain unaffected, i.e. the absence of side-effects, and why use of the composition does not change cancer cells (as observed visually) but renders them benign, and why metastasis is inhibited.

In cancer, toxic materials may indirectly affect a gene, leading to errors in nucleic acid translation and to errors in the cell. Provision of component (i) may allow the cell or its components to function normally. Genes that are responsible for differentiation may be corrected or, if not corrected, a suicide gene is unmasked, and lyses tumour cells.

In other genetic disorders, e.g. caused by viral infection, a foreign body interacts with the membrane or receptor, or enters the cell and causes local chemical or physical changes. A genetic disorder may be introduced or a genetic abnormality may be present. The present invention can prevent the virus from penetrating the cell membrane, or can destroy the virus. An abnormality in the membrane or receptor can be corrected. A normalised cell is not susceptible to the virus which is then destroyed by phagocytosis, stimulated and enhanced by opsonisation.

DETAILED DESCRIPTION OF THE INVENTION

The first of the given components of a composition of the invention is an antioxidant. The function of this component may be to prevent the formation of S—S bridges by oxidation of cysteine residues. Disulfide linkages are caused by many oxidising agents, and cause loss of enzymatic activity. Alternatively or in addition, the antioxidant may inhibit the production of oxygen radicals (free radicals) as a by-product of the normal metabolism of oxygen. These oxygen radicals are very damaging to cell membranes, proteins, lipids and DNA. Oxidative damage accumulates with age and is considered to be a major contributor to ageing and the development of degenerative diseases (e.g. cancer, cardiovascular disease, immune system decline, etc).

Suitable antioxidants for use in the invention are small molecules such as vitamin C, A and E. It will be appreciated that a suitable precursor of any such compound may be used, e.g. β-carotene. The preferred antioxidant for use in this invention is vitamin C, e.g. as ascorbic acid. A suitable dosage of this component is 1 to 500 mg/kg/day.

Alternatively or in addition, the first material that may be an essential component of a medicament according to the invention, typically comprises one or more components of vitamin B. Many enzymes catalyse reaction of their substrates only in the presence of a specific non-protein molecule, i.e. a coenzyme. Coenzymes frequently contain B vitamins as part of their structure. One or more of vitamins B1 (thiamine hydrochloride), B2 (riboflavin sodium phosphate), PP (nicotinamide), B6 (pyridoxine hydrochloride) and B5 (dexpanthenol) may be used. The amount of each such component is, for example, 0.1 to 50 mg/kg/day.

A second material that may be an essential component of a medicament according to the present invention is a metal salt that provides metal ions, in vivo. The nature of the anion is not critical, and will generally be chosen to be non-toxic and of suitable solubility or other appropriate compatibility with other components of the medicament. Many metal ions act as positive modifiers, and certain enzymes require the presence of metal ion for full activity. The function of the metal ion may be to complement the coenzyme. The ion may be, for example, Na, K or multivalent such as Fe, Mo, Mg, Mn, Ca, Zn, Cu or Co. This may be in the form of a salt, of which many examples are known, e.g. with any inorganic acid such as HCl or $H_2SO_4$, or an organic acid such as acetic, citric, gluconic, glutamic, maleic, malic or succinic acid. A preferred component of this type is calcium gluconate. A typical dosage of this component is 1 to 1000 mg/kg/day.

The third material that may be an essential component of a medicament according to the invention may be an agent that increases the permeability of cell membranes or otherwise enhances transport, e.g. by action on receptors. This material may enhance the ability of the cells that need treatment to receive the other active material or materials that may be included in the novel medicament, especially in human therapy (it may not be required in veterinary medicine). A preferred agent of this type is insulin or a growth hormone. A typical dosage of insulin is 1 to 1000 IU/kg/day.

The third material that may be an essential component of a medicament of the invention may also comprise an antihistamine. Such a material can not only prevent or reduce abnormal reactions, especially allergic reaction, but also prevent the accumulation of substances which block transport, e.g. by binding to cell membrane receptors.

As is known to those of ordinary skill in the art, antihistamines work by competing with histamine released by mast cells and basophils for histamine receptors on the mucosa of the eyes, nose, bronchial airways and skin. The antihistamine binds to the receptor and prevents histamine attachment, thereby blocking the effect of histamine in the tissues. Antihistamine drugs counteract the physiological effects of histamine production, in allergic reactions and colds.

Antihistamines can be divided into classical and non-sedating antihistamines. There are many examples of such compounds, including acrivastine, azatadine, azelastine, brompheniramine, carbinoxamine, cetirizine, chlorpheniramine, clemastine fumarate, cyproheptadine, diphenhydramine, doxepin, hydroxyzine, fexofenadine, loratadine, meclizine, phenindamine, promethazine, pyrilamine and tripolidine.

A preferred material for use in the invention is chlorpheniramine maleate. A suitable dosage of such a component is 0.1 to 50 mg/kg/day.

As is conventional in medicine, a medicament of the invention may comprise other components, depending on the intended effect, the nature of the formulation, the route of administration, and other factors that are known to those skilled in the art. Thus, for example, the medicament may be formulated in water, e.g. to provide an aqueous solution or suspension suitable for injection. It may be desirable to include in any such formulation one or more additional substances that aid dissolution or suspension of active components, such as an organic or a polar solvent. The composition may comprise conventional excipients, for example, phenol (which acts as a preservative).

It may be desirable to include an anti-irritant. It has been found that these effects can both be provided by the use of natural substances, e.g. the dried flower heads of the composite plant Matricaria chamomile or one or more materials therein, including volatile oils, azolene, anthemic acid, apogenin, glycosides and other substances. Azolene has antiphlogistic properties, abates allergic reactions, and intensifies regenerative processes. Apigenin (4',5,7-trihydroxyflavone) has a strong spasmolytic effect. Flavones reverse capillary fragility; such a component can inhibit abnormal chemical transmitters.

Compositions of the invention can be formulated by methods known to those skilled in the art. Pharmaceutically acceptable components should be used. The term "pharmaceutically acceptable" refers to those properties and/or substances which are acceptable to the patient from a pharmacological/toxicological point of view and to the manufacturing pharmaceutical chemist from a physical/chemical point of view regarding factors such as formulation, stability, patient acceptance and bioavailability.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients such as, for example, inert diluents such as calcium carbonate, sodium carbonate, lactose, calcium phosphate or sodium phosphate; granulating and disintegrating agents, for example corn starch or alginic acid; binding agents, for example starch, gelatin or acacia; and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated, to form osmotic therapeutic tablets for control release.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions may contain the active materials in admixture with suitable excipients. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents, for example a naturally occurring phosphatide such as lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, such as a polyoxyethylene with partial esters derived from fatty acids and hexitol anhydrides, for example polyoxyethylene sorbitan monooleate. Aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents (such as those set forth above) and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified above. Sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated using suitable dispersing or wetting agents and suspending agents, examples of which have been mentioned above. A sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition may also be administered in the form of suppositories for rectal administration of the drug. Such compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, suitable compositions are in the form of, for example, creams, ointments, jellies, solutions or suspensions. For the purposes of this specification, topical application includes mouth washes and gargles.

As indicated above, composition of the invention may be given by injection. Intramuscular injection is preferred, although any parenteral administration is suitable.

It may also be preferred that the composition is given orally. In this case, and in the event that the permeability-increasing agent is used, insulin should not be included in an oral formulation. Oral administration may be particularly preferred for veterinary medicine.

Other active materials may also be given to the subject. Although it is not believed that further materials are necessary, it has been found that certain steroids and vitamins, typically given orally, can support or enhance the effect of the medicament. Suitable steroid hormones may increase the synthesis of specific proteins, by unmasking certain cistrons, with the assistance of essential metabolites such as vitamins and amino acids. Examples of suitable steroids are estradiol, nandrolone and estriol. Vitamins such as A, D and/or E may also be given. The function of vitamin A may be to preserve the integrity of epithelial tissue, to play a role in protein synthesis, and to stabilise cell membranes and also subcellular membranes.

A composition of the invention may have cosmetic use, since it has been found that, when used as a medicament, hair growth can be restored or induced. For this purpose, a topical composition may be preferred.

Therapeutic uses of a composition according to the invention involve the treatment (and possibly also the prevention) of conditions described above. These and others include topical conditions such as psoriasis, scleroderma and pemphigus, infectious bronchitis, cancers including sarcomas (such as Kaposi's sarcoma), leukemia, skin cancer and the carcinomas whose treatment is specifically illustrated below, as well as AIDS. For the treatment of leukemia, the composition may be supplemented by the administration of a growth hormone. More generally, it may be used for therapy of proliferative and viral conditions, especially those associated with DNA or RNA viruses. The action on RNA viruses may be direct, while the action on DNA viruses and cancer at least may be progressive. The medicament may also be useful in therapy of other genetic disorders such as motor neurone disease and multiple sclerosis.

In the treatment of cancer, it has been found that the medicament may promote the patient's quality of life, without necessarily reducing tumour size. For example, it facilitates a healing process that has the following stages:

(i) metastasis and tumour growth cease (and the tumour mass may begin to decrease); and
(ii) the tumour is converted to a hard consistency by a process of fibrosis, and is isolated from surrounding normal tissue, which allows the tumour to be easily removed by surgery.

It appears that the medicament affects the immune system indirectly, by normalising body cells. It apparently has both direct and indirect effects in its anti-viral activity, demonstrated by its very rapid direct action on RNA viruses and by its direct and indirect action on DNA viruses and cancers. It apparently normalises otherwise abnormal genetic material; the effect may be both chemical and functional. It also appears that most of the cellular components become targets of the medicament, especially cell surface receptors and genetic material. Despite the effect on cells, no adverse side-effects have been detected, even after treatment for more than 18 months in cancer patients.

For the treatment of AIDS, the patient may have the human retrovirus (HRV); this indicates human immunodeficiency virus type I, or strains thereof apparent to one skilled in the art, which belong to the same viral families and which create similar physiological effects in humans as various human retroviruses.

Patients to be treated include those individuals (1) infected with one or more strains of a human retrovirus, as determined by the presence of either measurable viral antibody or antigen in the serum, and (2) having either a symptomatic AIDS-defining infection such as (a) disseminated histoplasmosis, (b) isopsoriasis, (c) bronchial and pulmonary candidiasis including pneumocystic pneumonia, (d) non-Hodgkin's lymphoma or (e) Kaposi's sarcoma or having an absolute CD4 lymphocyte count of less than 200/mm$^3$ in the peripheral blood.

Patients who are HIV-positive but asymptomatic would typically be treated with lower doses. ARC (AIDS-related complex) and AIDS patients would typically be treated with higher doses.

As may possibly be desired, components used in this invention can be administered in conjunction with (or simultaneously, concomitantly or sequentially with) other antiviral agents such as AZT, ddI, ddC, 3TC, d4T or non-nucleoside anti-AIDS agents.

Treatment of AIDS, as described herein, refers to inhibition of the HIV virus and will vary, depending on the infected individual. For individuals who are HIV-positive (infected) but who are asymptomatic, the medicament may delay or prevent the onset of symptoms. For individuals who are HIV-positive and symptomatic, and are pre-AIDS or ARC patients, the medicament may delay or prevent the onset of "full-blown AIDS". For individuals who have "full-blown AIDS", the medicament may at least considerably extend the survival time of these individuals.

The medicament can also be used to treat other viral conditions. For example, the virus may be a coronavirus, as in the case of SARS (severe acute respiratory syndrome). Further, as indicated above, it may have utility in veterinary medicine, e.g. in fowl's diseases such as Newcastle disease and fowlpox.

Although some indication has been given as to suitable dosages of certain materials, the exact dosage and frequency of administration depend on several factors. These factors include the particular components that are used, the particular condition being treated, the severity of the condition, the age, weight and general physical condition of the particular patient, and other medication the individual may be taking, as is well known to those skilled in the art.

Specific embodiments of the invention include:

E1. A composition comprising:
(i) a vitamin;
(ii) a metal salt that provides metal ions in vivo; and
(iii) insulin or a growth hormone.

E2. A composition according to embodiment E1, wherein the metal ions are Ca ions.

E3. A composition according to embodiment E1 or embodiment 2, which comprises vitamin C.

E4. A composition according to any preceding embodiment, which comprises a vitamin B compound selected from vitamins B1, B2, PP, B5 and B6.

E5. A composition according to any preceding embodiment, which additionally comprises an antihistamine.

E6. A composition according to any preceding embodiment, which additionally comprises camomile or an active component thereof.

E7. A composition according to embodiment E6, wherein said active component is apigenin.

E8. A composition according to any preceding embodiment, which comprises insulin.

E9. A composition according to any preceding embodiment, which additionally comprises phenol.

E10. A composition according to embodiment E9, which comprises an insulin-phenol complex.

E11. A composition according to any preceding embodiment, for therapeutic use.

E12. A composition according to embodiment any of embodiments E1–E10, or E11, which is an aqueous composition suitable for injection.

E13. A composition according to embodiment E11, which is adapted for oral administration, and which does not contain insulin.

E14. Use of the components defined in any of embodiments E1 to E10, for the manufacture of a medicament for use in therapy of a genetic disorder. In this embodiment, the invention is a method for treating a genetic disorder which comprises administering to a patient in need of such treatment an effective amount the components of embodiments E1 to E10.

E15. Use of one or more of the components defined in any of embodiments E1 to E10, for the manufacture of a medicament for use in therapy of a skin disease. In this embodiment, the invention is a method for treating a skin disease which comprises administering to a patient in need of such treatment an effective amount the components of embodiments E1 to E10.

E16. Use according to embodiment E15, wherein the disease is selected from psoriasis, scleroderma and pemphigus.

E17. Use of one or more of the components defined in any of embodiments E1 to E10, for the manufacture of a medicament for use in therapy of cancer. In this embodiment, the invention is a method for treating a cancer which comprises administering to a patient in need of such treatment an effective amount the components of embodiments E1 to E10.

E18. Use of one or more of the components defined in any of embodiments E1 to E10, for the manufacture of a medicament for use in therapy of AIDS. In this embodiment, the invention is a method for treating AIDS which comprises administering to a patient in need of such treatment an effective amount the components of embodiments E1 to E10.

E19. Use of one or more of the components defined in any of embodiments E1 to E10, for the manufacture of a medicament for therapy of a disease caused by a RNA or DNA virus, or a retrovirus. In this embodiment, the invention is a method for treating a disease caused by a RNA or DNA virus, or a retrovirus which comprises administering to a patient in need of such treatment an effective amount the components of embodiments E1 to E10.

E20. Use of one or more of the components defined in any of embodiments E1 to E10, for the manufacture of a medicament for therapy of a disease caused by a coronavirus. In this embodiment, the invention is a method for treating a disease caused by a coronavirus which comprises administering to a patient in need of such treatment an effective amount the components of embodiments E1 to E10.

E21. Use according to embodiment 19 or embodiment 20, wherein the disease is a fowl's disease.

E22. Use of one or more of the components defined in any of embodiments E1 to E10, as a cosmetic.

The invention is illustrated further by the following examples which are not to be construed as limiting the invention or scope of the specific procedures or compositions described herein. One skilled in the art will recognize that modifications may be made in the invention without deviating from the spirit or scope of the invention.

EXAMPLE 1

Medicament

The following substances were formulated:

| | | |
|---|---|---|
| 1. Dried flower heads of the composite plant Matricaria chamomile | 100 | g |
| 2. Pyrogen-free distilled water | 2.0 | Liter |
| 3. Phenol | 7.5 | ml |
| 4. Ascorbic acid (Vitamin C) | 27500 | mg |
| 5. Calcium gluconate (ionized calcium) | 75625 | mg |
| 6. (Insulin) a neutral solution of biosynthetic insulin | 750 | IU |
| 7. Chlorpheniramine maleate | 1250 | mg |
| 8. Vitamin B1 (thiamine hydrochloride) | 1250 | mg |
| 9. Vitamin B2 (riboflavin sodium phosphate) | 683.75 | mg |
| 10. Vitamin PP (nicotinamide) | 5000 | mg |
| 11. Vitamin B6 (pyridoxine hydrochloride) | 500 | mg |
| 12. Vitamin B5 (dexpanthenol) | 750 | mg |

Two liters of pyrogen-free distilled water were poured into a large beaker that was previously cleaned and washed with pyrogen-free distilled water and sterilized in an oven at 125° C. for one hour.

The dried flower heads of the composite plant Matricaria chamomile were washed thoroughly with cold pyrogen-free distilled water. The washed flower heads were added to the water in the beaker and heated and stirred until the temperature reached 95° C.

When the temperature was close to 35° C., the contents of the beaker were filtered through three layers of filter paper (previously washed with absolute ethanol). The filtrate was collected in another sterile pyrogen-free beaker. Calcium gluconate and ascorbic acid (Vitamin C) were added to the beaker and stirred. Again, the contents of the beaker were then filtered through three layers of filter paper (which was previously washed with absolute ethanol). The 7.5 ml of carbolic acid, preheated to 65° C. (its melting point is 63° C.) was added to the contents of the beaker and stirred well. When the temperature was close to 10° C., the vitamins B1, B2, PP, B6 and B5 (Becozyme), chlorpheniramine maleate (Allerfin) and neutral solution of biosynthetic insulin were added to the contents of the beaker and stirred well.

The resultant medicament was poured into small vials or ampoules of 5.0 ml or large vials or bottles of 100 ml or 50 ml of the type used for intravenous fluids. This medicament was suitable for use as an injectable.

A preferred process for preparing a camomile extract is as follows:

Camomile flowers of suitable quality, i.e. not too dry, are gently pressed through a 850 mm screen to remove dust and pick out green leaves. After discarding dust and particles, the flower heads retained by the screen are rubbed between the hands to release the yellow particles from the heads. The particles are then passed through a 850 mm screen to remove large bits of unwanted flower heads, and screened again three times through a 850 mm screen, shaking vigorously from side to side, to leave behind the lighter unwanted fraction. The resulting fraction is yellow in colour and slightly shiny.

To 100 g of the fraction is added approximately 2 liters of pyrogen-free sterile water for injection in a 3-liter clean glass beaker, and mixed by stirring. The product is heated using a hot plate to 95° C., then allowed to cool to approximately 35° C. The extraction mixture is sieved through a 355 mm screen to remove particles. The filtrate is passed through a 0.2 µm sterile filter, to give the desired liquid camomile extract.

THERAPEUTIC EXAMPLES

The medicament described above was given as a 5 ml dosage, intramuscularly, twice daily (5 ml every 12 hours) for an average body weight of 75 kilograms (subjects 50–100 kg body weight). The dose can be calculated, according to the body weight, as 0.072 ml/kg body weight twice daily.

Estradiol (5 mg) and Vitamin A (40000 IU) were given separately every week. In addition, estriol (0.5 mg) was given separately to the patient every day. Finally, nandrolone decanoate (Deca durabolin) (25 mg) was given separately to the patient every 20 days.

In various healthy animal and human models, this regimen has proved to be safe. Therapy according to the present invention has been successful in a number of cases. These include patients of the following types:

a. Patients with cancer at its terminal stages.

b. Patients with different types of viral disease.

c. Patients with diseases of genetic disorder oetiology, other than cancers, such as psoriasis, pemphigus, progressive systemic sclerosis, subacute sclerosing panencephalitis (SSPE) in children and motor neurone disease.

Specific patients that have been treated are 10 independent patients having the following conditions:

(1) adenocarcinoma of the head of the pancreas with metastasis to the regional lymph nodes and also to the liver, with a large cyst in the body of the pancreas (100×125 mm); metastasis to most of the skeletal regions; exudative moist scales all over the skin, diagnosed as eczema herpetica; ascites.

(2) follicular carcinoma of the thyroid with metastasis to the right iliac bone; following treatment, the metastasis increased to include greater trochanter of the right thigh, the skull and other parts of the skeleton including the left vertebrae.

(3) poorly differentiated squamous cell carcinoma of the mandible.

(4) poorly differentiated malignant lymphoma of the lymphatic type, or lymphosarcoma.

(5) cerebella astrocytoma (a well differentiated low grade cerebella astrocytoma, histologically grade 1–2).
(6) papillary transitional cell carcinoma of the urinary bladder, with metastasis all over the skeleton.
(7) pemphigus
(8) carcinoma of the head of the pancreas with multiple metastasis in the port a hepatis with obstruction of the biliary ducts intra- and extra-hepatic.
(9) progressive systemic sclerosis (scleroderma).
(10) squamous cell carcinoma of the laryngeal surface of the epiglottis and on the right vestibular folds (invasive squamous cell carcinoma of the supraglotic region with extension to the pre-epiglotic space and valleculae); limited movement of the right vocal cord (previous left side thoracotomy).

In the case of the patient with scleroderma, an anti-nuclear antibody test (using immunofluorescence) was positive before treatment, and negative afterwards.

The following are fuller case studies.

EXAMPLE A

The patient was male, 41 years old. According to the medical report of his surgeon, the patient presented to him with a history of obstructive jaundice with progressive weight loss, oedema of the legs, palpable gall bladder and ascitis with ascitic fluid. Ultrasound examination showed enlarged liver with dilated intra- and extra-hepatic bile ducts in addition to the gall bladder. The patient was operated on, and the findings were: advance carcinoma of the head of the pancreas, 50–75 mm in diameter, a large pancreatic cyst about 100–125 mm in diameter with secondaries in the regional lymph nodes, and a mass of 20×20 mm located in the inferior surface of the right lobe of the liver with dilated gall bladder and biliary ducts. Palliative procedures were carried out (side-to-side choledochoduodenostomy around T-tube splint and retrocolic gastrojejunostomy). The pathological report of the lymph nodes was metastatic adenocarcinoma. Chemotherapy was conducted, but without any benefit as the metastatic lesions increased, accompanied by health deterioration and severe emaciation.

When treated according to the invention, the patient became progressively better, and all the tumours of the pancreas, liver, lymph nodes, other viscera, the bones and other parts of the body disappeared. The ascitic fluids vanished, and the skin returned to normal within 2 months. The patient was cured completely after 15 months of treatment.

EXAMPLE B

The patient was an 8 year old male child, diagnosed as having a tumour in the occipital region of the brain. The tumour was excised and examined histopathologically; it was a well differentiated low grade cerebellar astrocytoma, histologically grade 1–2. After excision of the tumour, an intra-cranial catheter was introduced in the intraventricular space for drainage. The patient was then discharged and given deep X-ray therapy, but his general health deteriorated. Death was anticipated.

When treated according to the invention, the child's general health progressively improved, and the hair of the scalp regrew. After a period of one year, all examinations and investigations proved that the patient was cured completely. 5 years' later, he was normal.

EXAMPLE C

The patient was a woman, 45 years old. She underwent operation of the osteolytic lesions which were found in the radiographs at the right iliac bone just above the acetabulum. Histopathological examination of a sample taken from the lesion showed a metastatic follicular carcinoma in the bone consistent with an origin in thyroid gland. The patient was treated by iodine radiotherapy, but metastatic lesions appeared in the greater trochanter of the right femur and then in the skull. Thyroidectomy found no primary lesion. It was concluded that the primary lesion was occulted.

After treatment according to the invention, the lesions regressed gradually, and the bone matrix of the lesions regenerated everywhere after the regression of the tumour. The matrix of the new bone reformed, calcifications recurred, and the patient was cured completely. There has been no recurrence for more than 4 years, and the patient is now in good health.

EXAMPLE D

A male patient, 62, noticed increased mobility of the incisors of the lower jaw with swelling in the gum. Following consultation, he underwent complete extraction of his teeth from both jaws. A biopsy, done from tissues of the swelling in the incisors' region, examined histopathologically, showed a poorly differentiated squamous cell carcinoma. It was decided to remove the mandible of the lower jaw as, radiologically, multiple osteolytic lesions were found all over the bone. The patient refused insertion of an artificial (platinum) mandible.

After the commencement of treatment according to the invention, the patient's health progressively improved. The osteolytic lesions regressed, and the bone defect which resulted from the operation and the osteolytic lesions reformed by natural bone formation. Radiographs showed no remnants of the osteolytic lesions after about 5 months from the beginning of the treatment. Whole body skeletal survey, chest X-ray, ultrasound examination of the abdominal and pelvic viscera and all haematological and biochemical examinations of the blood proved normal. Complete recovery occurred within less than six months.

EXAMPLES E–G

Three patients with AIDS were treated.

The first patient exhibited persistent generalised lymphadenopathy (PGL) of many years' standing; severe weight loss; chronic blood diarrhoea of 10 years' history of remission and exacerbation which started due to ulcerative colitis; severe fatigue which rendered him unable to walk for several meters; and marked oral and lingual thrush (candidal stomatitis) with some papules at the cheeks which accompanied by severe symptoms of oesophageal candidiasus such as dysphagia.

These findings were accompanied by the following signs and symptoms: loss of appetite in addition to phagophobia due to severe oesophageal pain; deficiency in libido, accompanied by impotence; cachectic appearance; fungal infection of the left hand and both feet which caused noxious pruritus; fingernails that looked dirty, thickened, scaly, deteriorated and fragile due to tinea unguum infection; painful and tender hepatomegaly (liver enlarged to about four fingers below the right subcostal margin) of more than 2 years' duration; moderate chest pain during respiration at both mammary regions with retrosternal pain during swallowing even the fluids; and bad psychological feelings accompanied by insomnia.

The patient had been treated with Retrovir as an antiviral drug, other antiviral drugs and many antibiotics. He gained some benefits from the antiviral drugs for a short period. A relapse in his general health occurred during such treatment.

The second patient exhibited: PGL of a few years' duration; chronic serosanguineous-like urethral discharge; herpes zoster infection (shingles) of the penis, leading to huge lesions and to fistula formation; decrease in libido; and poor psychological state.

The third patient exhibited: breathlessness (some difficulties in breathing); fatigue; and a chronic abscess at the right side of the nose, over the lacrimal duct, 10 mm below the medial angle of the right eye. This abscess was not dissolved or cured by local and general usage of antibiotics and local antiseptics.

Following treatment according to the invention, for 4 weeks, all the given signs and symptoms disappeared, with some exceptions. Thus, the lymph nodes did not dissolve completely, but their size was reduced to about one-third, and they became soft instead of rubbery, and mobile instead of fixed to the underlying tissues. The fingernails that had deteriorated had not completely returned to normal, but new growth was free from fungal infection. The herpes vesicles of the penis subsided, reappeared twice only but without pain, then vanished completely without recurrence.

After 10 weeks, the lymph nodes disappeared completely. The fungal infection of the nails had disappeared, so that the new growing parts were very clean, healthy and shiny (without topical medication). The herpes vesicles had vanished without any recurrence.

Haematology

The neutrophils/lymphocytes ratio before treatment was 1:2. This ratio was monitored during the treatment; the ratio in the three patients became 2:1 which is almost the acceptable ratio.

Total counts for both neutrophils and lymphocytes returned to their normal range in the three patients.

Total WBC count, total T-lymphocyte count and T4-lymphocyte count all increased to the normal levels.

Systemic Biochemistry

After the treatment, the enzymes GOT (AST), GPT (ALT), alkaline phosphatase, acid phosphatase and serum amylase all decreased to their normal levels.

Immunoglobulins, especially IgG and IgA, also decreased to their normal ranges.

Antibody Serum Level

HIV antibody serum levels were assayed in the three patients, at different dates. The threshold value (relative fluorescent value) of the patients decreased successively, as follows:

|  | Time | | |
| --- | --- | --- | --- |
|  | 0 | 7 days | 3 months |
| First Patient | 33.1 | 29.5 | 22.7 |
| Second Patient | 36.6 | 32.5 | 21.7 |
| Third Patients | 26.3 | 22.2 | 20.2 |

HIV-RNA

For evaluation of the quantity of HIV-RNA, RT-PCR was used to investigate blood samples taken from the three patients just before the treatment and at many times thereafter.

After 70 days of treatment, HIV bands were detected at the same location of HIV-1 positive control bands. In one of the patients, the results showed a huge decrease in the viral RNA concentration to a very low level, at which its band could hardly be seen. In the other two patients, the viral load was reduced to only 50% of that obtained at the beginning of the treatment. Viral RNA concentrations decreased greatly.

A single dose acute toxicity test in rats has been completed. Male and female rats were randomly assigned to 25 µl intramuscular, single dose injections. 20 animals were studied. 5 rats/sex/group were dosed. They were sacrificed after 24 hrs and 14 days of injection.

Dose levels were chosen to mimic the dose being used in the patients treated so far. No toxic symptoms were reported in any of the animals studied. No mortality was reported in this acute phase. No macroscopic organ change or damage was observed during the necropsy in any of the animals. Body weight of the animals was not affected by the drug.

Assays

Preliminary results have shown that, in a tumour cell proliferation assay, the medicament inhibited growth of cancer cell lines in a concentration-dependent fashion (mean IC70:1.1 vol %). Selectivity was demonstrated for lung, breast and melanoma cancer cell lines.

In a tumour stem cell assay, the medicament inhibited growth of explanted human tumour cells in a concentration-dependent fashion (mean IC70:1.6 vol %). Selectivity was demonstrated for lung, breast and melanoma cancer, corroborating the results from the proliferation inhibition assay. Furthermore, significant growth inhibition was found for ⅔ pancreatic, ½ gastric and ¼ colon tumours.

It is to be understood that the foregoing describes preferred embodiments of the invention and that modifications may be made therein without departing from the spirit or scope of the invention as set forth in the claims.

The invention claimed is:

1. A composition comprising:
   (i) a vitamin C;
   (ii) a metal salt that provides metal ions in vivo;
   (iii) insulin or a growth hormone; and
   (iv) camomile or an active component thereof.

2. A composition according to claim 1, wherein the metal ions are Ca ions.

3. A composition according to claim 2, which comprises a vitamin B compound selected from vitamins B1, B2, PP, B5 and B6.

4. A composition according to claim 3, which additionally comprises an antihistamine.

5. A composition according to claim 4, wherein said active component is apigenin.

6. A composition according to claim 4, which comprises insulin.

7. A composition according to claim 6, which additionally comprises phenol.

8. A composition according to claim 7, which comprises an insulin-phenol complex.

9. A composition according to claim 4, which additionally comprises phenol.

10. A composition according to claim 8, which is an aqueous composition suitable for injection.

11. A composition according to claim 1, which is adapted for oral administration.

12. A composition according to claim 1, which comprises a vitamin B compound selected from vitamins B1, B2, PP, B5 and B6.

13. A composition according to claim 1, which additionally comprises an antihistamine.

14. A composition according to claim 12, which additionally comprises an antihistamine.

15. A composition according to claim 5, which comprises insulin.

16. A composition according to claim 1, which is an aqueous composition suitable for injection.

17. A composition according to claim 1, which is adapted for oral administration, and which does not contain insulin.

18. A pharmaceutical composition comprising:
(i) vitamin C;
(ii) a metal salt that provides metal ions in vivo;
(iii) insulin or a growth hormone; and
(iv) an antihistamine,
together with a pharmaceutically acceptable excipient.

* * * * *